(12) United States Patent
Yang et al.

(10) Patent No.: US 6,806,249 B2
(45) Date of Patent: Oct. 19, 2004

(54) PERFUME CONTAINING SURFACTANT COMPOSITIONS HAVING PERFUME BURST WHEN DILUTED

(75) Inventors: Lin Yang, Fort Lee, NJ (US); Judith Lynne Kerschner, Hawthorne, NJ (US)

(73) Assignee: Unilever Home & Personal Care USA, a division of Conopco, Greenwich, CT (US)

( * ) Notice: Subject to any disclaimer, the term of this patent is extended or adjusted under 35 U.S.C. 154(b) by 164 days.

(21) Appl. No.: 10/085,736

(22) Filed: Feb. 28, 2002

(65) Prior Publication Data

US 2003/0166499 A1 Sep. 4, 2003

(51) Int. Cl.[7] ................................. A61K 7/46
(52) U.S. Cl. ........................ 512/1; 512/2; 512/3
(58) Field of Search ........................... 512/1, 2, 3

(56) References Cited

U.S. PATENT DOCUMENTS

| | | | |
|---|---|---|---|
| 5,500,138 A | 3/1996 | Bacon et al. | |
| 5,540,853 A | 7/1996 | Trinh et al. | |
| 6,001,789 A | 12/1999 | Trinh et al. | |
| 6,143,707 A | 11/2000 | Trinh et al. | |

FOREIGN PATENT DOCUMENTS

| | | |
|---|---|---|
| GB | 2311296 A | 9/1997 |
| WO | 97/30688 | 8/1997 |
| WO | 00/24367 A | 5/2000 |

OTHER PUBLICATIONS

"Physiochemical Models of Flavor Release from Foods" de Roos, Kris, 2000 American Chemical Society, pp. 126–141.
International Search Report Application No. PCT/EP 03/01692 mailed Aug. 4, 2003.
J. Behan et al.: "Perfume interactions with sodium dodecyl sulphate solutions" International Journal of Cosmetic Science, vol. 9, No. 6, 1997, pp. 261–268, XP008019363.
J. N. Labows et al.: "Solubilization of Fragrances by Surfactants" Research & Developmet, Colgate–Palmolive Company, pp. 605–619, XP–002247379.

*Primary Examiner*—Jill Warden
*Assistant Examiner*—Monique T. Cole
(74) *Attorney, Agent, or Firm*—Ronald A. Koatz

(57) ABSTRACT

The present invention relates to compositions having a fragrance burst of at least 20% relative to a product before dilution. The composition is selected such that perfume and surfactant in said composition yields a calculated "Perfume Burst Index" (PBI) value of less than 3 as per algorithm defining the PBI.

9 Claims, 12 Drawing Sheets

Product Parameters that Influence Perfume Performance in Diluted PW Products

Figure 1: Product Parameters that Influence Perfume Performance in Diluted PW Products
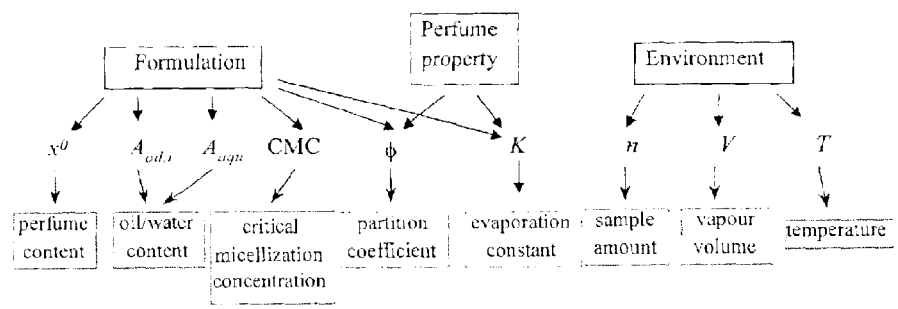

Figure 2: Theoretical Calculations of Fragrance Burst with Dilution
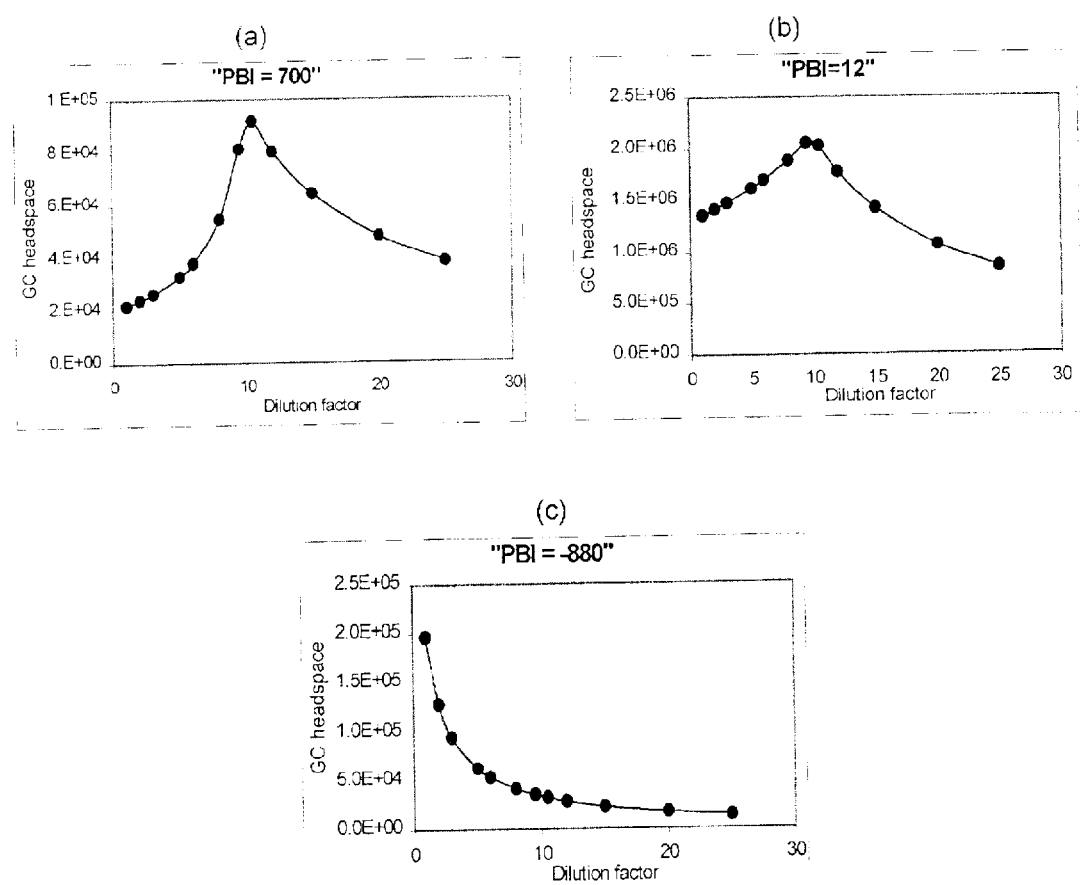

Figure 3: Fragrance Burst Profiles of Different Perfume Molecules in Surfactant Solution (5% sodium laurate solution)
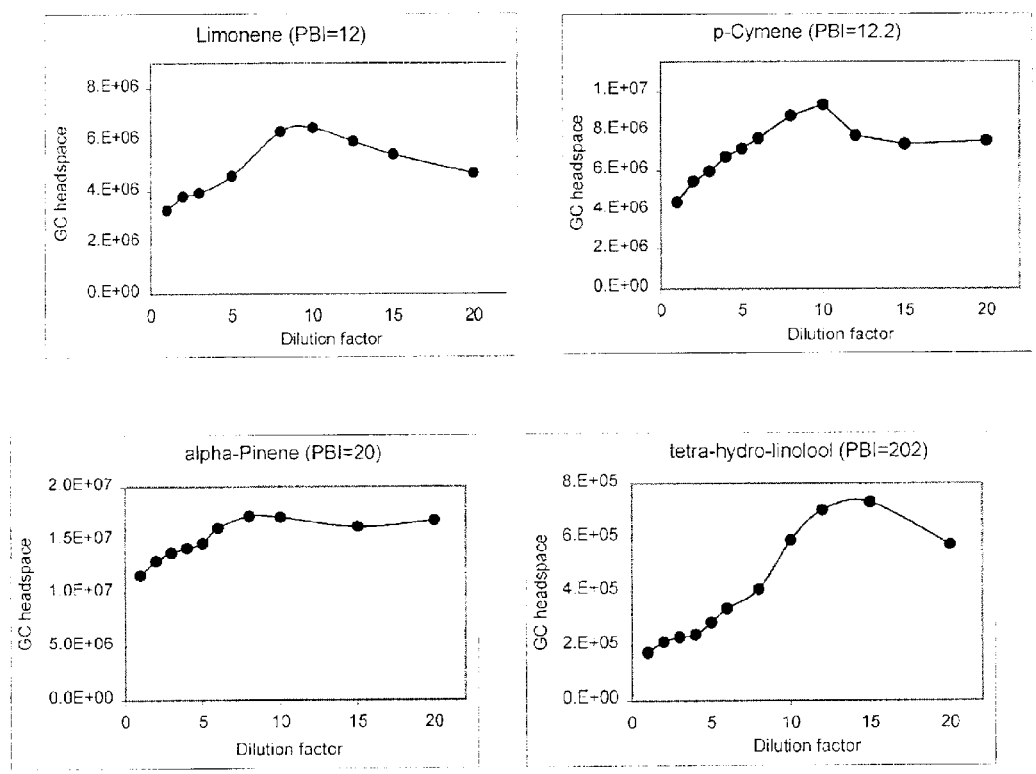

Figure 3: Fragrance Burst Profiles of Different Perfume Molecules in Surfactant Solution (5% sodium laurate solution) (Cont'd)
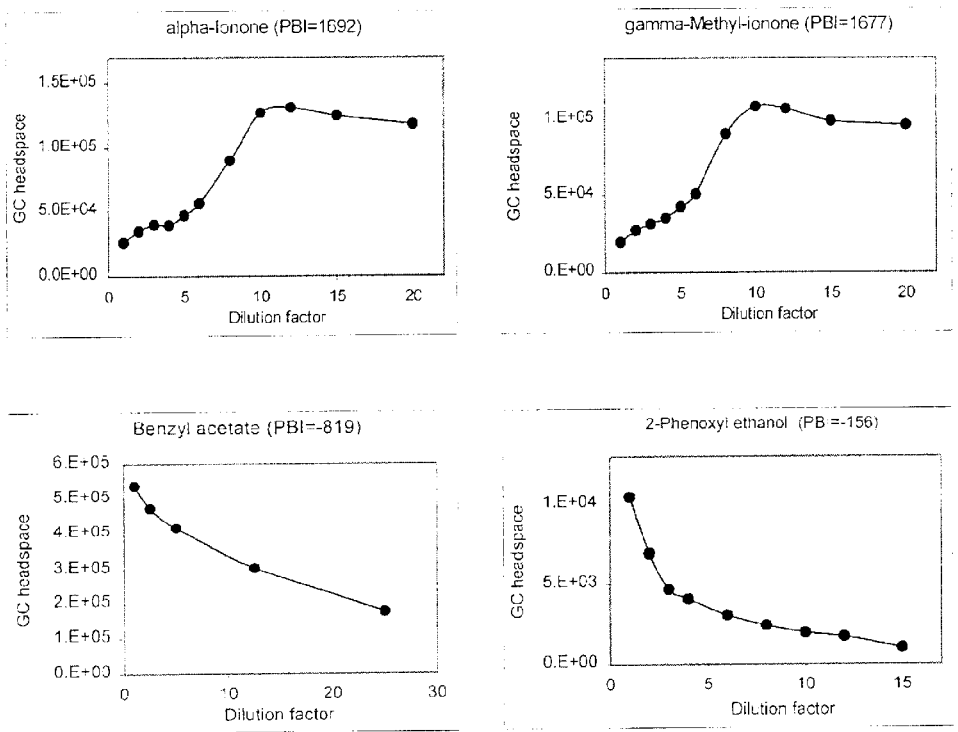

Figure 4: Two-components Fragrance in Shower Liquid that Change Note upon Dilution
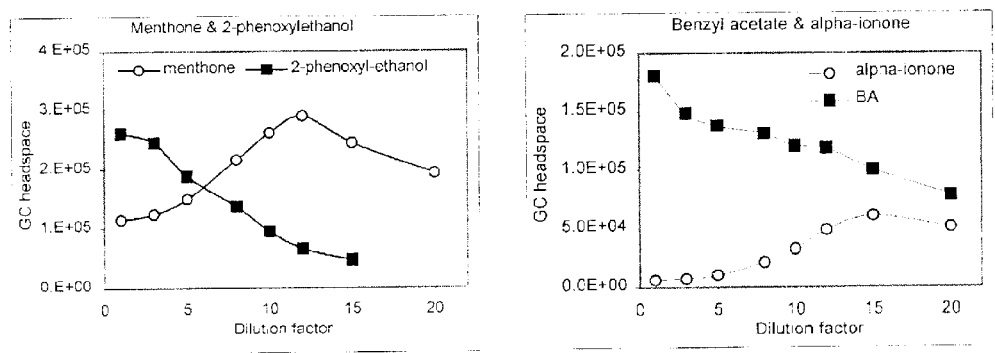

Figure 5: Theoretical Models of Fragrance Burst with Change in Surfactant Concentration
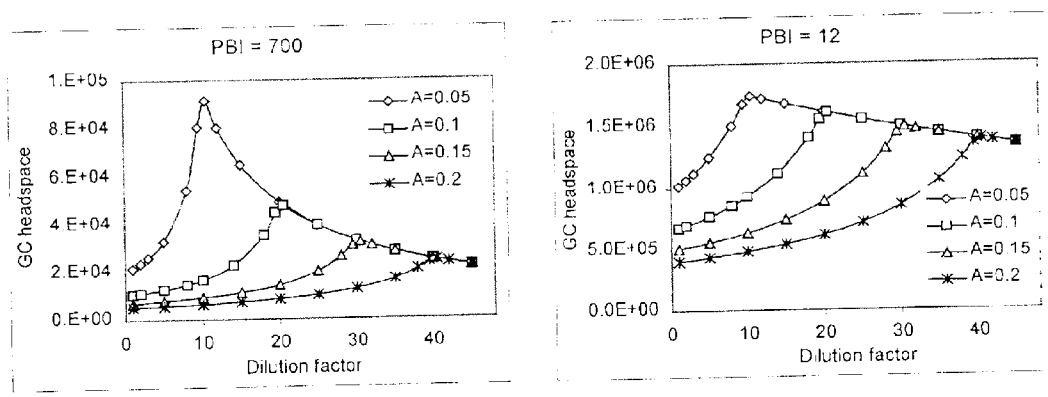
A: The concentration of the surfactant (wt/wt).

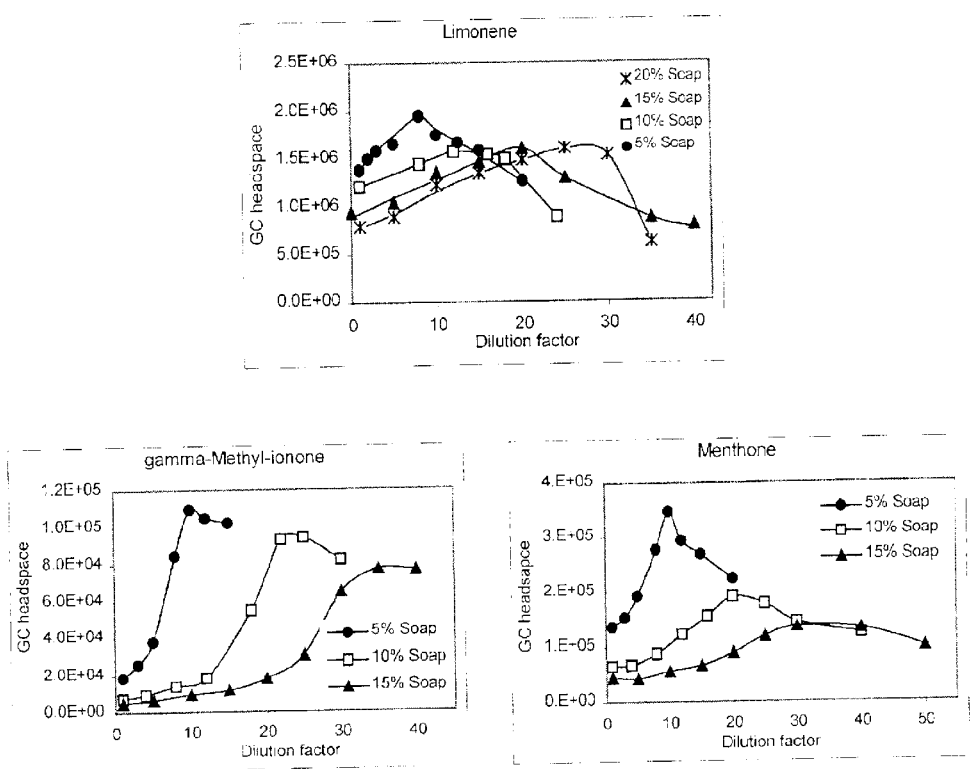
Figure 6: Experimental Results of Fragrance Burst with Changes in Surfactant Concentration

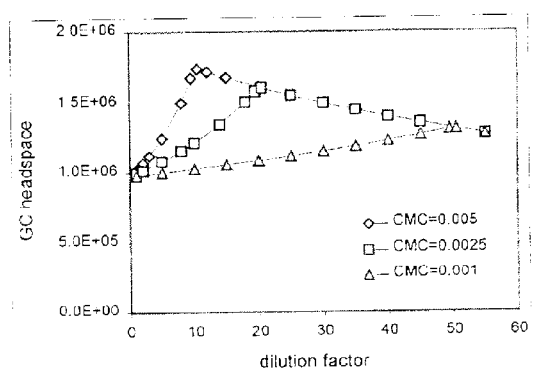
Figure 7: Theoretical Model of Fragrance Burst with Change in Surfactant CMC

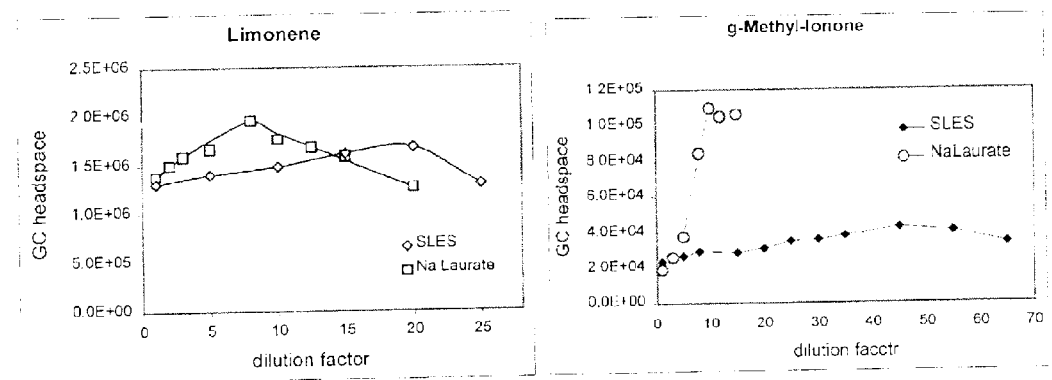
Figure 8: Experimental Results of Fragrance Burst with Change in CMC

Figure 9: Normalized Dilution Curve for Component in a Perfume Mixture
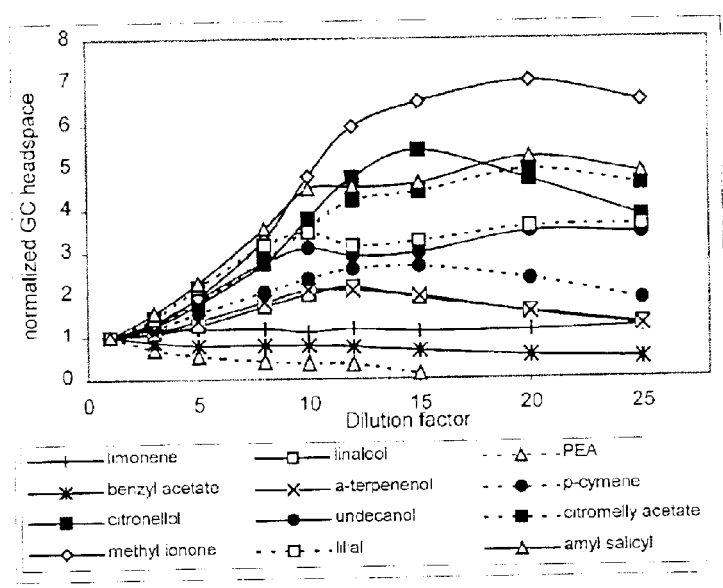

Figure 10: Results of Panel Study of the Single Perfume (γ-methyl-ionone) Systems
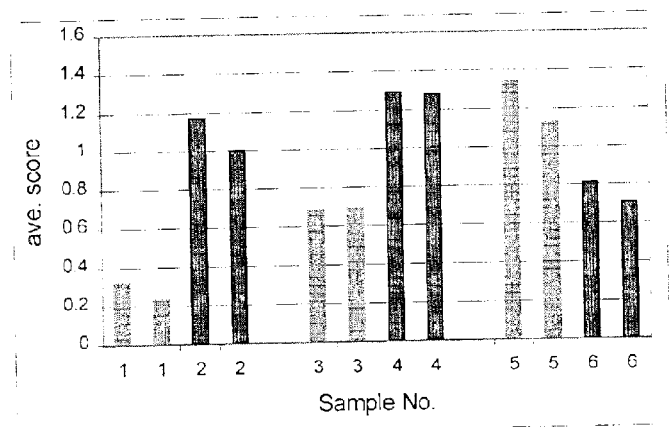

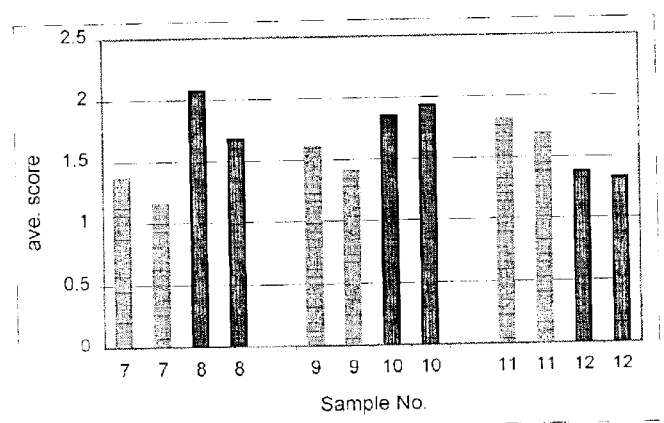
Figure 11: Results of Panel Study of the Multi-component Perfume (menthone, tetra-hydrol-linalool, α-ionone, γ-methyl-ionone) Systems

PERFUME CONTAINING SURFACTANT COMPOSITIONS HAVING PERFUME BURST WHEN DILUTED

FIELD OF THE INVENTION

The invention relates to compositions, e.g., personal wash perfume-containing compositions, which are able to deliver perfume benefits (i.e., "burst" or increase in perfume headspace relative to undiluted composition) upon dilution in water. More specifically, by being aware of which properties of the perfume and of the surfactant systems in which they are found are responsible for perfume release on dilution, applicants have been able to provide both specific compositions and processes for selecting perfumes and/or surfactant systems in said compositions which meet defined criteria (as defined, for example, in perfume burst index) and thereby provide aroma burst of at least defined levels upon dilution.

BACKGROUND OF THE INVENTION

Perfume is a key component for a favorable consumer experience with home and personal care products. It is also often the most costly component of the formulation. Typically most of the fragrance is quickly lost as the product is used because most of the perfume is trapped in the surfactant system. There has been a long-standing need to improve the utilization of perfumes and to design compositions that provide maximum and prolonged impact in use. It is one objective of this invention to develop a means by which products can be developed to provide greater fragrance impact and novel fragrance characteristics in use.

To this end, the applicant has found that perfume activity (e.g., the aroma of the perfume) both in a product (e.g., surfactant containing product) and upon use (e.g., dilution of product in shower) can be correlated to the thermodynamic characteristics of (1) the perfume itself and (2) the formulation in which the perfume is found.

For example, the degree to which a perfume will partition into oil or water (measured by a so-called "partition coefficient" and a reflection of the hydrophobicity of the perfume) and the degree to which the perfume evaporates (measured by "volatility constant" and a reflection of the volatility of the perfume) are two significant characteristics of the perfume which strongly affect the potential perfume "burst" when said product is diluted. By burst is meant an increase in the concentration of perfume in the vapor phase above the solution (i.e., this is also known as perfume headspace) with respect to the undiluted product and composition. The vapor phase can of course vary depending on product, for example, from a small area above a bottle of perfume to an area in a shower stall.

As noted, the perfume burst is affected not only by the perfume properties, but also by properties of the formulation in which the perfume is found. Thus, the number and type of surfactant micelles found in a surfactant solution also has an effect. For example, in a surfactant with high critical micellization concentration (CMC) (in compositions of high CMC, micelles do not form as readily) perfume "burst" would occur more readily and less dilution is required. The critical micellization concentration is defined as the surfactant concentration at which micelles begin to form from unassociated surfactant monomers (M. J. Rosen, Surfactants and Interfacial Phenomena, $2^{nd}$ Ed., 1989). Conversely, in a surfactant with low critical micelle concentration (e.g., one where micelles do form easily or, stated differently, don't break apart as readily once formed), a perfume, being generally more hydrophobic, tends to stay in the surfactant more readily. As a result, the perfume will tend not to "burst" (increase perfume headspace) as readily and, to achieve more headspace, more dilution may be required.

Other important formulation factors which may affect the "burst" of the perfume may include, but are not limited to, perfume content in solution and surfactant to water ratio.

Still another factor which can affect perfume "burst" is the environment in which it is found, e.g., such environmental factors as (1) overall sample amount; (2) vapor volume and (3) temperature.

According to the subject invention, applicants have succeeded in putting together a thermodynamic model which can be used to select the types of perfume and formulations which should be used in order to maximize this perfume burst or actual headspace (actual concentration of perfume in vapor phase) when a formulation (e.g., personal wash or shampoo formulation) is diluted in use.

More specifically, applicants have defined a perfume burst index which defines compositions which can deliver a perfume burst upon dilution of at least a certain amount relative to undiluted composition; and further allows applicants to define a process for obtaining such compositions.

In general, the burst is achieved by diluting a surfactant system (e.g., an aqueous surfactant system) where upon burst begins upon dilution and maximum burst is obtained upon reaching CMC, therefore, releasing all of the perfume from the surfactant system. Thus, a composition yielding a maximum fragrance burst of 20% means the perfume concentration in the headspace increases by about 20% relative to the undiluted product when the solution is diluted through the CMC. The CMC is the point where perfume-surfactant-water system changes to perfume-water system (i.e., system is too dilute for micelles to form).

A surfactant system is defined as a surfactant and/or surfactant mixtures which may include ingredients selected to manipulate the CMC in a continuous phase. These selected ingredients can include urea; glycerine; $C_1$–$C_{12}$ straight-chained or branched alcohols or diols; water soluble polymers such as polyvinylpyrolidone, polyvinylalcohol, polyethyleneglycol, polypropyleneglycol; multivalent electrolytes such as magnesium, calcium and aluminum salts; and sugars such as dextrose, glucose, maltose, galactose, sucrose. The continuous phase is typically water, but may also include $C_1$–$C_8$ straight-chained or branched alcohols or diols, glycerine, $C_1$–$C_8$ esters and combinations thereof.

Generally, surfactants which may be used include anionic, nonionic, amphoteric/zwitterionic and cationic surfactants as discussed in more detail below.

In one embodiment, the invention relates to a composition having a fragrance burst, as measured by a "perfume burst index", of about 20% relative to a composition containing surfactant systems and perfume/fragrance prior to dilution of said product.

More specifically, the invention relates to specific compositions obtained by selecting perfume and/or perfumes and surfactant systems and/or mixtures of surfactant systems and calculating therefrom a perfume burst index (PBI) according to the following formula:

$$PBI = \frac{\phi - 1.4/CMC}{K}$$

wherein $\phi$=oil/water partition coefficient of selected perfumes or perfume components in a mixture;

CMC=critical micellization concentration of surfactant systems or mixture of surfactant systems (wt./wt.);

K=volatility constant of perfume or perfume components in a mixture from the continuous phase (atmospheres); and The perfumes and surfactant systems are specifically selected to ensure that the PBI calculated is greater than about 3.

It should be understood that the PBI defines the maximum potential fragrance burst which is achieved at the CMC for the surfactant or surfactant mixture. For example, a relatively low PBI (e.g., about 3) will obtain a "burst" of at least 20% as noted. However, if the PBI is higher, much higher fragrance burst can be expected. Thus, for example, a burst of 20% may be achieved upon immediate dilution (assuming high enough PBI) and may continue to 700% or 800% or more at CMC (which as noted is point of maximum potential burst).

As far as applicants are aware, there is no art which specifically discloses that such burst can be obtained with such compositions or which discloses a way of predicting when and under what circumstances such fragrance "burst" will occur based on the dilution behavior of a perfume-surfactant-water system. Further no art of which applicants are aware discloses how such compositions are in turn related, for example, to properties of the perfume (e.g., partition coefficient, volatility) as well as to properties of the formulation (e.g., surfactant concentration and surfactant CMC).

BRIEF SUMMARY OF THE INVENTION

The invention relates to surfactant compositions, preferably aqueous surfactant compositions (e.g., bars, personal wash liquids, shampoos) in which perfume and surfactant are selected as to provide a fragrance burst, when diluted, of at least about 20% relative to undiluted product. Compositions must have a perfume burst index, as defined, of about 3.0 or greater, preferably 4.0 or greater.

The invention further relates to a process for selecting such compositions by selecting perfumes and choosing surfactant system or manipulating CMC of surfactant system to ensure the PBI is at least about 3.0.

The invention is based on applicants' observation that variations in perfume impact ("burst") on dilution are essentially caused by the competition between a decrease in overall fragrance concentration upon dilution; and an increase in fragrance concentration in the continuous phase as the fragrance is released during disassociation of surfactant micelles which occurs during dilution. More specifically, and without wishing to be bound by theory, applicants have observed and shown that only perfumes with relatively large oil/water partition coefficient (very hydrophobic) possess the potential to produce a fragrance burst upon dilution. Other parameters which are important to minimum burst include (1) volatility constant of perfume; (2) surfactant concentration; (3) type of surfactant system; (e.g., CMC) etc.

Specifically, applicants have developed a theoretical mathematical equation based on the various variables noted above. More specifically, they have developed a perfume burst index which both defines compositions having a maximum burst of at least 20% and further provides a process for selecting such compositions based on properties of perfume and surfactant system.

The relationships are defined in more detail below.

BRIEF DESCRIPTION OF THE INVENTION

FIG. 1 is a chart showing various product parameters that influence perfume performance in diluted products (e.g., diluted personal wash products).

FIG. 2 shows theoretical calculation of fragrance burst for 3 types of perfume (as per Table 1) with dilution.

FIG. 3 shows fragrance burst profiles of different perfumes in surfactant solution.

FIG. 4 discloses an example of 2-component fragrances which would change note upon dilution as one component increases in concentration and another decreases.

FIG. 5 shows theoretical models of fragrance burst with changes in surfactant concentration.

FIG. 6 shows experimental results of fragrance burst with changes in surfactant concentration FIG. 7 shows theoretical model of fragrance burst with change in surfactant CMC.

FIG. 8 shows experimental results of fragrance burst with change in surfactant CMC.

FIG. 9 shows normalized dilution curve for component in a perfume mixture.

FIG. 10 shows result of sensory scores averaged overall panelists in a panel study of single perfume.

FIG. 11 shows results of sensory scores averaged over all panelists panel study of multi-component perfume.

DETAILED DESCRIPTION OF THE INVENTION

According to the subject invention, applicants have identified surfactant compositions in which perfume and/or perfumes and surfactant system and/or surfactant systems are selected to provide a fragrance burst when diluted. The burst is at least 20% at dilution although it can be much higher and reaches maximum strength at CMC. Applicants have further developed a process for determining (using defined perfume burst index) how to identify these compositions. That is, when a perfume is in a perfume-surfactant-water system (where some portion of perfume will be associated with surfactant micelles and some portion will be in water) and the formulation is diluted, a fragrance "burst" is produced when parameters are properly chosen. The intensity of the burst will depend, for example, on how much of the perfume is released from micelles as dilution occurs; and on the volatility of the perfume.

More specifically, some factors which affect perfume headspace concentration, upon dilution, are (a) various perfume properties (e.g., oil/water partition coefficient; $\phi$, which is a measurement of the partitioning of the perfume or of the perfume components in a mixture between the oil and water phases, thereby reflecting the hydrophobicity of perfume; and volatility constant, K, which is a measure of the partial pressure of the perfume or of the perfume components in a mixture in the vapor phase above the continuous phase of the composition, thereby reflecting the volatility of the perfume); (b) surfactant concentration in formulation (e.g., lower surfactant concentration tends to result in higher perfume headspace over initial formulation and more intense "burst" around CMC with fewer required dilutions); and (c) CMC of surfactant system (e.g., higher surfactant system CMC tends to provide more intense fragrance "burst" around CMC with fewer required dilutions).

As noted earlier, in general, for a fragrance "burst" or increase in perfume headspace concentration to occur during product use, the amount of fragrance released from micelles as they dissociate must compensate for overall decrease in perfume concentration upon dilution. Compositions having a Perfume Burst Index (PBI) greater than about 3 clearly meet the necessary criteria.

Typically, a cleansing composition (e.g., a personal wash cleansing composition) containing perfume can be thought of as a perfume-oil-water system with the oil phase comprising surfactant micelles and water forming the continuous phase. Any perfume will distribute between the surfactant micelles and water phase as governed by the perfume's surfactant/water partition coefficient. In addition, the equilibrium perfume headspace concentration is proportional to the perfume concentration in the aqueous phase as governed by the volatility constant, K. The presence of a surfactant micelle phase impacts perfume headspace concentration by solubilizing the perfume and thereby affecting perfume concentration in the aqueous phase (e.g., more in micelles, less is in the water).

Use of, for example, a personal wash cleansing product in bath or shower causes dilution. This dilution leads to a decrease in micelle concentration forcing the perfume into the aqueous phase and, accordingly, affecting the headspace concentration or perfume "burst".

However, dilution causes the quantity of surfactant micelles in a surfactant composition to decrease until gradually reaching critical micellization concentration (CMC). Below CMC, surfactant is present only as monomers or other small aggregates not large enough to form micelles. At this point, all perfume which was previously present in micelles is totally released.

More specifically, it should be understood, CMC is the point of maximum potential burst (e.g., where release of perfume is complete because there are no more micelles). The release of perfume, however, begins as soon as dilution occurs and the burst gradually increases from first dilution up until CMC.

In measuring perfume headspace (using, for example, gas chromatography headspace measurement), applicants observed that dilution of certain compositions containing perfume or perfume components in a perfume mixture led to an increase in perfume headspace and that, upon reaching the CMC, maximum perfume headspace was achieved. It is precisely this "burst" or increase in headspace (e.g., from start of dilution up until CMC) and methods for determining in what compositions it will occur that is the basis of the subject invention.

The different parameters that affect perfume concentration in the vapor phase can be controlled by manipulating the formulation, the perfume itself or the environment in which the product dilution is occurring as shown in FIG. 1. Understanding how each variable affects the overall fragrance performance in a personal product composition in use is critical to designing optimum systems for enhanced perfume benefits (e.g., fragrance burst, enhanced perfume deposition).

More specifically, applicants have found compositions which yield a maximum fragrance burst of at least about 20%, relative to undiluted product. These compositions are defined by establishing a perfume burst index (PBI) which is defined below:

$$PBI = \frac{\phi - 1.4/CMC}{K}$$

wherein $\phi$=oil/water partition coefficient of perfume or perfume components in a mixture;
CMC=critical micellization concentration (wt./wt.) of surfactant systems;
K=volatility constant of perfume or perfume components in a mixture from the continuous phase (atmospheres);
wherein variables are selected such that PBI is greater than about 3.

As noted, perfume headspace behavior of a perfume-surfactant-water system is governed by different thermodynamic principles above or below CMC upon dilution. The perfume headspace behavior upon dilution is closely related to the oil/water partition coefficent ($\phi$) and the volatility constant (K) of perfume, which reflect the hydrophobicity and volatility of the perfume respectively.

In Table 1 below, perfumes are classified into four categories according to their oil/water partition coefficients ($\phi$) and their volatility constants (K). Since two of the three factors contributing to the PBI value for fragrance molecules are the partition coefficient and volatility constant, one can predict the extent of "perfume burst" these different types of perfume should exhibit in the proper surfactant system.

TABLE 1

Classification of Perfume Molecules

|  | Examples of Partition Coefficient $\Phi$ (log$\Phi$) | Hydrophobicity | Examples of Volatility Constant K* | Volatility | Initial headspace | Burst upon dilution |
| --- | --- | --- | --- | --- | --- | --- |
| For Perfume Type 1 | 50 (1.7) | Low | 50 | High | Very high | No |
| For Perfume Type 2 | 1000 (3) | High | 1 | Low | Very low | High |
| For Perfume Type 3 | 1000 (3) | High | 250 | High | High | Medium |
| For Perfume Type 4 | 50 (1.7) | Low | 1 | Low | Low | No |

*K is generally measured in units of atmosphere.

Fragrance molecules that fall into the Type 1 category are actually very rare, but due to their low partition coefficient ($\phi$) and their high volatility constant, one would predict no fragrance burst upon dilution. The low solubility in the surfactant phase would result in very small release of fragrance upon dilution, so a typical dilution profile (e.g., where perfume headspace decreases continuously with dilution) would be expected. That is, such molecules would normally tend to be found in the water phase anyway. So any action (dilution) causing release of perfume from surfactant micelles would be largely irrelevant.

In general, type 1 perfumes have oil/water partition coefficient ($\phi$) of 1 to about 200, preferably 2 to 100; and volatility constant (K) of 2 to 1000, preferably 50 to 1000 atmospheres.

Type 2 perfumes would be anticipated to produce the most intense "perfume burst" upon dilution. These molecules are typically fragrance base notes and are very hydrophobic although their overall volatility is low resulting in low fragrance impact in a typical full formulation, i.e., before dilution. Therefore upon dilution, these molecules are released from the surfactant micelles and the noted increase in fragrance intensity is quite large. That is, because of their hydrophobicity, the perfume molecules tend to stay in micelles until release upon dilution and this release combined with the low volatility of the perfume in the initial formulation causes a high burst. In general, Type 2 perfumes have oil/water partition coefficients greater than 500, preferably greater than 700 and volatility constant less than about 20, preferably less than about 15.

Specific examples of Type 2 perfume molecules include allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl acetate, citronellyl isobutyrate, citronellyl propionate, cuminic aldehyde, cyclohexylsalicylate, cyclamen aldehyde, cyclomyral, dihydro isojasmonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super™ (7-acettl,1,2,3,4,5,6,7,8-octahydro,1,1,6,7-tetramethyl napthalene), cis-jasmone, lilial, linalyl benzoate, 20 methoxy naphthaline, methyl cinnamate, methyl eugenol, γ-methylionone, methyl linolate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara and ylangene.

Hydrophobic, volatile fragrances fall into the Type 3 perfume category. Since these molecules have high oil/water partition coefficients, they will be solubilized by the surfactant system and then be released upon dilution providing a "perfume burst". The actual extent of this burst will not be as large as that for Type 2 perfumes because the fragrances are so volatile in the first place, hence the PBI values will be lower, but great enough to provide a perceivable burst. In general, they will have an oil/water partition coefficient of greater than about 500, preferably greater than 700; and a volatility constant of about 20 to 1000.

Type 3 fragrance molecules fall into the top and middle note categories and include allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, and verdox.

Finally, Type 4 perfume components which again are classified as top and middle notes, have very low oil/water partition coefficients and therefore like Type 1 components would not be expected to release significantly upon dilution to provide a "perfume burst". While these molecules will not add to the intensity of the fragrance burst in a fully formulated perfume, they are still very important fragrance components. By combining perfume molecules that decrease in intensity upon dilution with those that "burst" upon dilution, the overall fragrance note during use will change. Fragrance note is defined as the type of odor a perfume or mixture of perfume components produces. For example, phenethylalcohol provides a floral rose note, methylionone produces a woody note, and bergomot and limonene produces citrusy, fruity notes. The fragrance could smell different in-use to that of the original product. Typically these perfumes will have an oil/water partition coefficient of about 1 to about 200, preferably 2 to 100 and a volatility constant of less than about 20, preferably less than about 15.

Fragrance Type 4 molecules include acetanisol; amyl acetate; anisic aldehyde; anisylalcohol; benzaldehyde; benzyl acetate; benzyl acetone; benzyl alcohol; benzyl formate; hexenol; laevo-carveol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde); dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline; ligustral; linalool oxide; methyl acetophenone; methyl amyl ketone; methyl anthranilate; methyl benzoate; methyl benzyl acetate; methyl heptenone; methyl heptyl ketone; methyl phenyl carbinyl acetate; methyl salicylate; octalactone; para-cresol; para-methoxy acetophenone; paramethyl acetophenone; phenethylalcohol; phenoxy ethanol; phenyl acetaldehyde; phenyl ethyl acetate; phenyl ethyl alcohol; prenyl acetate; propyl butyrate; safrole; vanillin and viridine.

In general, as noted above, it can be seen that molecules with higher oil/water partition coefficient (e.g., Type 2 and 3) will have a greater burst. This may be, without wishing to be bound by theory, because the perfume is highly soluble in the surfactant micelles and upon dilution, which triggers the dissociation of these micelles, a large amount of perfume is released thereby compensating for the decrease in overall perfume concentration in the diluted system. As noted from perfume Type 3 versus 2, this is balanced to some extent by volatility (volatility constant) of the perfume since, for two perfumes otherwise having same partition coefficient, the one which is less volatile (Type 2) will be expected to have larger burst.

The CMC of the surfactant system also affects "perfume burst". Thus, for example, a surfactant system of relatively low CMC (e.g., sodium lauryl ether sulfate, also known as SLES) lowers the PBI and can greatly reduce the expected "perfume burst" on dilution. By contrast, surfactant systems of relatively higher CMC (e.g., sodium laurate compared to SLES) would raise PBI and can thus increase "perfume burst" on dilution. Examples of CMC for various individual surfactants are set forth in Table 2 below.

TABLE 2

The Critical Micellization Concentration (CMC) of Surfactants

| Surfactant | CMC (wt./wt.) |
|---|---|
| $C_8H_{17}SO_3^-Na^+$ | 0.0346* |
| $C_{10}H_{21}SO_3^-Na^+$ | 0.0105* |

TABLE 2-continued

The Critical Micellization Concentration (CMC) of Surfactants

| Surfactant | CMC (wt./wt.) |
|---|---|
| $C_{12}H_{25}SO_3^-Na^+$ | 0.0034* |
| $C_8H_{17}SO_4^-Na^+$ | 0.0325* |
| $C_{10}H_{21}SO_4^-Na^+$ | 0.00858* |
| $C_{11}H_{23}SO_4^-Na^+$ | 0.00438* |
| $C_{10}H_{21}OC_2SO_3^-Na^+$ | 0.00452* |
| $C_6H_{13}OOCCH_2SO_3^-Na^+$ | 0.0412* |
| $C_8H_{17}OOCCH_2SO_3^-Na^+$ | 0.0181* |
| $C_8H_{17}OOC(CH_2)_2SO_3^-Na^+$ | 0.0132* |
| $C_{12}H_{25}OOC(CH_2)_2SO_3^-Na^+$ | 0.0132* |
| $C_{12}H_{25}OOC(CH_2)_2SO_3^-Na^+$ (SCI) | 0.00076* (30° C.) |
| $C_4H_9OOCCH_2CH(SO_3^-Na^+)COO\ C_4H_9$ | 0.0664* |
| $C_5H_{11}OOCH_2(SO_3^-Na^+)COO\ C_5H_{11}$ | 0.0178* |
| $C_6H_{13}OOCCH_2CH(SO_3^-Na^+)COO\ C_6H_{13}$ | 0.0053* |
| $n\text{-}C_6H_{13}(OC_2H_4)_6OH$ | 0.0271* |
| $(C_2H_5)_2CHCH_2(OC_2H_4)_6OH$ | 0.0366* |
| $(C_3H_7)_2CHCH_2(OC_2H_4)_6OH$ | 0.0091* |
| $C_6H_{13}[OCH_2CH(CH_3)]_2(OC_2H_4)_{9.9}OH$ | 0.0307* |
| n-octyl-β-D-glucoside | 0.0111* |
| Pluronic $EO_{37}PO_{58}EO_{37}$ | 0.0065** |
| Sodium laureth sulfonate (2EO) (50° C.) | 0.0011*** |
| Sodium laureth sulfonate (3EO) (50° C.) | 0.00084*** |
| Linear alkylbenzene sulfonate | 0.00171*** |
| Sodium oleate | 0.0008*** |
| Potassium laurate | 0.00607*** |
| Sodium laurate | 0.0052*** |
| Caprylamidopropyl betaine | 0.00032 |

Reference:
*M. J. Rosen, Surfactants and Interfacial Phenomena, 2$^{nd}$ ed., 1989
**P. Alexandris, L. Yang, Macromolecules, 2000, 33, 5574–5587.
***P, Mukerjee, K. J. Mysels, Critical Micelle Concentrations of Aqueous Surfactant Systems, 1971

The CMC of the surfactant or surfactant system mixture can itself be manipulated (e.g., to help control "perfume burst") by using various components which can be added to affect the CMC.

Non-limiting examples of such component include urea; glycerine; $C_1$–$C_{12}$ straight-chained or branched alcohols or diols; water soluble polymers such as polyvinylpyrolidone, polyvinylalcohol polyethylene glycol, or polypropyleneglycol, multivalent electrolytes (e.g., magnesium, calcium and aluminum salts); and sugars such as dextrose, glucose, maltose, galactose and sucrose.

In general, the surfactant system or surfactant system mixture are selected to have a CMC greater than about 0.0001 (wt./wt.).

In general, however, there is no limitation to the surfactant or surfactant system which can be used. That is, the surfactant system of the invention may comprise anionic, nonionic, amphoteric/zwitterionic and/or cationic surfactant and/or mixtures of any of these. That is, the invention is not dependent on type of surfactant system, but only on CMC of surfactant or surfactant systems.

Among anionic surfactants which may be used are included aliphatic surfactants (e.g., non-limiting examples include $C_8$ to $C_{22}$ alkane sulfonate or disulfonate, alkene sulfonate, hydroxy alkane sulfonate, alkyl glyceryl ether sulfonate); and aromatic sulfonate (e.g., alkyl benzene sulfonate).

Also included are alkyl sulfates (e.g., $C_{12}$–$C_{18}$ alkylsulfate); alkyl ether sulfates; alkyl sulfosuccinates; alkyl and acyl taurates; alkyl and acyl sarcosinates; sulfoacetates; alkyl phosphates; phosphate esters; acyl lactates; $C_8$ to $C_{22}$ monoalkyl succinates and maleates; sulfoacetates; and acyl isethionates. Also included are carboxylates. Salts of anionic surfactant (also known as fatty acid soaps) may also be included.

Zwitterionic surfactants can be broadly described as derivatives of aliphatic quaternary ammonium, phosphonium and sulfonium compounds in which aliphatic radicals can be straight or branched chain and wherein at least one aliphatic substituent contains about 8 to about 18 carbons and at least one contains an anionic group, e.g., carboxy, sulfonate, sulfate, phosphate or phosphonate.

Amphoteric surfactants include at least one acid group (e.g., carboxylic or sulfonic). They include quaternary nitrogen and may include quaternary amido acids as acid group. They also generally include alkyl or alkeny group of 7 to 18 carbons. Example include simple betaines, amido betaines and sulfobetaines.

Nonionic surfactants which may be used include reaction product of compounds having a hydrophobic group and a reactive hydrogen (for example, aliphatic alcohols, acids, amides or alkyl phenols) with alkylene oxide, especially ethylene oxide either alone or with propylene oxide. Examples include alkylphenols-ethylene oxide condensates and condensation products of aliphatic ($C_8$–$C_{18}$) primary or secondary linear or branched alcohols with ethylene oxide. They may also be sugar amides and alkylpolyglycosides.

Cationic surfactants include quaternary ammonium compounds such as, for example, alkyldimethyl ammonium halogenides.

Some examples of surfactants which may be used in surfactant systems of the invention include sodium lauryl ether sulfate, sodium laurate, potassium lauride, sodium oleate, potassium oleate, triethanolamine laurate, alkylpolyglucosides, sodium lauryl sulfate, caprylamidopropyl betaine and sodium cocoylisethionate. As noted, however, there is theoretically no limit as to which surfactant or surfactant systems may be used.

In another embodiment, the invention relates to a composition wherein fragrance note can be changed subsequent to dilution by (1) selecting a fragrance with a mixture of perfume components wherein some have PBI greater than 3.0 and some have PBI less than 3.0; and (2) assuring selection of fragrance components such that the components desired in the new fragrance (i.e., notes with desired fragrance after dilution) have a PBI greater than about 3.

In yet another embodiment, the invention relates to a composition wherein a desired fragrance note can be subsequent to dilution by ensuring that fragrance or fragrance components having the desired aroma and which are selected for the composition have a PBI greater than about 3 so that, upon dilution, the perfume headspace concentration exceeds the odor threshold. Odor threshold is the minimum concentration of fragrance in the vapor phase required for human detection.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Example 1

Fragrance molecules vary quite a bit in their physical properties and can therefore provide a variety of different effects depending on properties such as hydrophobicity, water solubility, volatility, molecular weight, etc. As shown in Example 1, some perfume components with specific physical parameters will provide a "fragrance burst" upon dilution of surfactant containing products such as shampoos, shower gels, soap bars, etc. A "perfume burst index" has been developed to determine which fragrance molecules will provide a burst or an increase in perfume in the air upon dilution of the product (which typically happens during standard use of shampoos, shower gels, soap bars, light duty liquids, etc.). This "perfume burst index" (PBI) is a function of several physical properties of the perfume and of the surfactant system. Depending on the amount of fragrance burst one desires, certain PBI is required.

$$PBI = \frac{\phi - 1.4/CMC}{K}$$

$\phi$=oil/water partition coefficient of selected perfume or perfume components of a mixture;

CMC=critical micellization concentration (wt/wt) of surfactant system;

K=volatility constant of perfume or perfume components of the mixture from the continuous phase To achieve a small, but potentially noticeable maximum fragrance burst of 20% from a product containing surfactant, the PBI of the perfume should be greater than about 3.0. To produce a 50% enhancement of the fragrance, the PBI needs to be greater than about 11 and to double the amount of fragrance upon use, the PBI should be greater than about 27. A "perfume burst index" can be calculated for any desired perfume molecule in a surfactant system. Table 3 contains a list of fragrance molecules and their PBI's in a product with CMC of 0.005 wt/wt (i.e. sodium laurate).

TABLE 3

PBI Values for Various Perfumes

| Perfume Molecule | PBI | "20% Burst"? |
|---|---|---|
| Acetanisol | −31,000 | No |
| p-Cresol | −27,778 | No |
| Indole | −5,209 | No |
| Benzyl Acetate | −819 | No |
| 2-Phenoxyethanol | −156 | No |
| 2-heptanone | −153 | No |
| Acetaldehyde | −130 | No |
| Cinnamyl Acetate | −122 | No |
| Hexanal | −109 | No |
| Methyl Benzoate | −13 | No |
| Anisole | −5 | No |
| Limonene | 12 | Yes |
| p-Cymene | 12.2 | Yes |
| α-pinene | 20 | Yes |
| Isoeugenol | 58 | Yes |
| Menthone | 61 | Yes |
| Naphthalene | 107 | Yes |
| 2-Nonanone | 180 | Yes |
| Tetrahydrolinolool | 202 | Yes |
| Linalool | 240 | Yes |
| Dihydromyrcenol | 307 | Yes |
| Nonanal | 502 | Yes |
| Ethyl Undecylenate | 624 | Yes |
| Decanal | 942 | Yes |
| α-ionone | 1,692 | Yes |
| γ-methyl ionone | 1,677 | Yes |
| 1-nonanol | 24,164 | Yes |
| Methyl Linolenate | 771,304 | Yes |
| Methyl Linoleate | 61149428 | Yes |

Example 2

As noted in Table 1 of the specification, perfume may have various properties depending on hydrophobicity oil/water (oil/water partition coefficient), volatility (volatility constant), etc.

FIGS. 2(a)–2(c) show calculated fragrance concentration profile in the headspace for three different types of perfume in a 5% surfactant product containing surfactant system with a CMC of 0.5% (i.e., sodium laurate). Hence, maximum fragrance burst is obtained with 10 dilutions (around CMC). FIG. 2(a) is "type 2" perfume (high hydrophobicity, low volatility), where one would expect high burst at CMC; FIG. 2(b) is "type 3" perfume (high hydrophobicity, high volatility), where burst at dilution is less than for Type 2; and FIG. 2(c) is "type 4" perfume (low hydrophobicity, low volatility), where no "burst" would be expected.

In general, fragrances with high "perfume burst index" (PBI) will produce much larger burst upon dilution than those with medium PBI. Perfume molecules with PBI less than about 3 will essentially produce no perceivable enhancement in smell on dilution and simply show standard dilution curve with decreasing perfume concentration in headspace (see FIG. 2(c)).

In general, it may be noted that one key to "burst" is that the perfume must have high hydrophobicity.

Example 3

Several different fragrance molecules were tested experimentally to validate the theoretical predictions. Limonene, p-cymene, α-pinene, tetrahydrolinolool, α-ionone, γ-methyl ionone, benzyl acetate and 2-phenoxylethanol were tested in a 5% sodium laurate shower product and diluted a number of times through the CMC (FIG. 3). The PBI of limonene is 12, p-cymene is 12.2, α-pinene is 20, tetrahydrolinolool is 202, α-ionone is 1692, γ-methyl ionone is 1677, benzyl acetate is −819 and 2-phenoxylethanol is −156. As predicted, limonene, p-cymene and α-pinene with a moderate positive PBI show moderate fragrance bursts of ~95%, 120% and 50% respectively. Tetrahydrolinolool, α-ionone and γ-methyl ionone with large PBI values give quite large fragrance bursts of 320%, 430% and 460%, while benzyl acetate and 2-phenoxylethanol with low, negative PBI values show no fragrance burst at all.

Example 4

Besides simply obtaining a "fragrance burst" upon dilution of these surfactant containing products, one can also produce a change in fragrance note. Many perfumes are a combination of many different fragrance molecules. Depending on the combination of molecules and the amount of each fragrance component in the mixture, one can obtain both a "fragrance burst", i.e. an overall increase in fragrance concentration in the air around the product, and/or a change in fragrance note, i.e. a change from a "floral/green" note to a citrus note. The reason this change in fragrance note can be obtained is because upon product dilution, those molecules with a PBI greater than 3 will actually increase in concentration while those compounds with a PBI less than 3 will simply dilute and decrease in concentration. Therefore the concentration of the different fragrance components smelled with product use will change from that smelled over the fully formulated "original" product and hence the overall character or "note" of the fragrance will be modified.

A few examples of fragrance mixtures that would be predicted to change note upon product dilution or use are shown in Tables 4–5. FIG. 4 shows examples of two 2-component fragrances which would definitely change note upon dilution as one component increases in concentration and the other decreases.

TABLE 4

Perfume that Could Change "Note" on Dilution in Surfactant Containing Product

| Fragrance Component | PBI | Dilution Behavior |
|---|---|---|
| Benzyl Acetate | −881 | Decrease headspace (HS) |
| Cinnamyl Acetate | −43.3 | Decrease HS |
| Limonene | 12 | Increase HS (50%) |
| Dihydromycenol | 86 | Increase HS (>3 times) |
| a-ionone | 366 | Increase HS (>3 times) |

TABLE 5

Perfume that Could Change "Note" on Dilution in Surfactant Containing Product

| Fragrance Component | PBI | Dilution Beahavior |
|---|---|---|
| 2-heptanone | −153 | Decrease HS |
| Menthone | −71.4 | Decrease HS |
| Isoeugenol | 58 | Increase HS (>3 times) |
| Tetrahydrolinalool | 202 | Increase HS (>3 times) |
| Linalool | 240 | Increase HS (>3 times) |

Example 5

It is also possible to take advantage of the technology of the invention to provide the introduction of a smell during dilution of the surfactant containing product. This can be achieved by formulating a fragrance ingredient into the product at a concentration just below the odor threshold. Therefore this component will not be perceived by the consumer in the original product, but as dilution occurs, if the PBI is large enough to supply a concentration of that component into the headspace above the product to exceed the odor threshold, the fragrance molecule will now be perceived upon use.

This concept can be used to provide a product that is essentially "fragrance-free", but produces a light fragrance with product dilution. This concept can also be utilized to change fragrance note, but providing a new smell upon product dilution to combine with the other perfume molecules to produce a new overall perfume mixture with use.

Example 6

As suggested by the theoretical predictions, formulation factors also play a role in controlling the fragrance burst from the surfactant containing product in use. Two very important factors are the surfactant concentration in the original product and the CMC of the surfactant mixture used in the formulation The effect of surfactant concentration can be predicted from the theoretical predictions in Example 1. The charts in FIG. 5 show the result of two different perfumes with PBI of ~700 and ~12 with varying surfactant concentration (surfactant CMC=0.005 wt/wt). As the graphs indicate, with a lower surfactant concentration in the original formulation, the initial fragrance concentration above the product will be higher (e.g., because fewer fragrance molecules are in surfactant micelles) and maximum fragrance burst can be reached with fewer dilutions. This is especially important, because the actual amount of dilution that typically occurs during product use is variable depending on the type of product and the consumer's habits. If the fragrance burst occurs with minimal dilution, the effect is more likely to be noticed by the product user. The other distinct advantage of products with low surfactant levels is that the absolute amount of fragrance available during the fragrance burst is greater, therefore the consumer will experience more fragrance during product use.

Example 7

Experiments performed on actual perfumes in products with different surfactant concentrations are shown in FIG. 6. Limonene (PBI=12.2) was tested in shower liquids containing sodium laurate at 5, 10, 15 and 20 wt.%, γ-Methyl Ionone and menthone were tested in sodium laurate at 5, 10 and 15 wt.% (FIG. 6). As noted in the theoretical calculations in Example 6, the maximum fragrance burst is reached with fewer dilutions in the 5% soap product and the overall amount of fragrance available during the burst is also greater for the 5% product.

Thus, as seen, lower surfactant concentration is highly beneficial.

Example 8

As noted in Examples 2 and 6, another variable that affects the fragrance burst properties of a formulation is the critical micellization concentration (CMC) of the surfactant system. The CMC is actually used to calculate the PBI for various fragrance molecules. As the CMC of the surfactant system is decreased, the PBI values for different fragrance molecules also decreases as shown in Table 6. Therefore in products with surfactant systems with low CMC values, the expected extent of the fragrance burst for different fragrances will be less.

TABLE 6

Fragrance Burst Potential in Surfactants with Different CMC's

| Fragrance | PBI CMC = 0.005 | Burst | PBI CMC = 0.0025 | Burst | PBI CMC = 0.001 | Burst |
|---|---|---|---|---|---|---|
| Benzyl Acetate | −819 | No | −1694 | No | −4319 | No |
| Hexanal | −109 | No | −268 | No | −599 | No |
| Methyl Benzoate | −13 | No | −32 | No | −89 | No |
| 2-Octanone | −5 | No | −178 | No | −697 | No |
| Isoeugenol | 58 | Yes | 21 | Yes | −90 | No |

TABLE 6-continued

Fragrance Burst Potential in Surfactants with Different CMC's

| Fragrance | PBI CMC = 0.005 | Burst | PBI CMC = 0.0025 | Burst | PBI CMC = 0.001 | Burst |
|---|---|---|---|---|---|---|
| Hexyl Acetate | 86 | Yes | −119 | No | −188 | No |
| Napthalene | 107 | Yes | 78 | Yes | −10 | No |
| 2-Nonanone | 194 | Yes | −94 | No | −190 | No |
| Linanool | 240 | Yes | 147 | Yes | −133 | No |
| Limonene | 12 | Yes | 9 | Yes | 1 | No |
| α-Ionone | 1692 | Yes | 1261 | Yes | −30 | No |
| α-Pinene | 20 | Yes | 19 | Yes | 16 | Yes |
| Tetrahydrolinolool | 202 | Yes | 183 | Yes | 127 | Yes |
| Dihydromyrcenol | 307 | Yes | 267 | Yes | 145 | Yes |
| Ethyl Undecylenate | 624 | Yes | 557 | Yes | 357 | Yes |
| Decanal | 942 | Yes | 916 | Yes | 847 | Yes |
| Methyl linolenate | 771304 | Yes | 771283 | Yes | 771222 | Yes |

As expected, the lower the CMC of the surfactant systems, the lower the fragrance burst potential. Also, since the CMC is lower and the maximum burst is found around the CMC, as one moves to products with lower CMC's, the consumer will have to dilute the product more to actually experience higher fragrance concentrations.

Example 9

Limonene and γ-Methyl Ionone were tested in two different shower liquid samples. One product was formulated with 5% sodium laurate (CMC=0.005 wt/wt) and the second with 5% sodium laureth sulfate (CMC=0.0011 wt/wt) (FIG. 8). These results validate the theoretical results in FIG. 7. The product with the lower CMC gives a lower overall fragrance burst and more dilutions are required to reach the maximum burst potential.

Example 10

A typical fully formulated perfume used in a commercial product, e.g., personal wash formulation, usually is a multi-component composition in which the properties of each perfume component can vary dramatically. A typical perfume mixture in a 5 wt. % sodium laurate formulation was tested for its "perfume burst" behaviour upon dilution. The PBI values of the components in this perfume mixture vary from a large negative number (e.g., benzyl acetate, PBI=−819; PEA, PBI=−200 in sodium laurate solution) to a large positive number (e.g., gamma-methyl-ionone, PBI=1,677 in sodium laurate solution). The dilution behaviour of each component in this perfume mixture is shown in FIG. 9 (the graph represents a normalized GC measurement so the amount of burst of each molecule is clearly indicated). In this perfume mixture of twelve components, the dilution behaviour of each component is different. Each component has a unique dilution curve (GC headspace vs. dilution factor) governed by the factors (hydrophobicity, volatility, etc) discussed previously. For instance, for those perfumes with a negative PBI (e.g., benzyl acetate), the perfume headspaces decrease upon dilution. For those perfumes with a moderate positive PBI (e.g., limonene, PBI=12; p-cymene=12.2 in sodium laurate solution), the perfume headspaces increases 1–2 times upon dilution. For those fragrance components with a very large positive PBI (e.g., gamma-methyl-ionone), the "perfume burst" can be as high as seven times. The results shown in FIG. 9 indicated that in a fully formulated perfume, in terms of dilution behaviour, the performance of each component is mostly determined by its own individual physical properties.

Example 11

Trained sensory panel analyses were carried out to validate the "perfume burst" phenomena. A group of 20 to 30 expert sensory panellists were asked to rate the intensity of the fragrance over formulations and anchor their scores to a perfume standard supplied for each test. Formulations containing a single perfume (gamma-methyl-ionone) and multi-component perfume were studied in two separate panels. The multi-component perfume contains four perfumes of equal weight percentage, menthone, tetra-hydro-linalool, α-ionone, γ-methyl-ionone, that will all "burst" in a sodium laurate product, but will not "burst" (e.g., menthone, α-ionone) or will give a moderate "burst" (e.g., tetra-hydro-linalool, γ-methyl-ionone) in an SLES product with dilution. Each sample was tested in duplicate and the sample information and the panel study results are shown in Tables 7 and 8, and FIGS. 10 and 11. As shown in Tables 7 and 8, perfumes at two different initial concentrations were tested in the sodium laurate solution. The scores shown in FIGS. 10 and 11 are the panel averages for each sample.

The results of the panel analyses indicate that as expected, both the single perfume and the perfume mixture (FIGS. 10 and 11) in a sodium laurate product (a surfactant of high CMC, CMC=0.5 wt. %), have higher sensory scores for the 10 times diluted solution compared to the original undiluted formulations. In the SLES formulations (a surfactant of relatively low CMC, CMC=0.1 wt. %), both single perfume and perfume mixture (FIGS. 10 and 11) have lower sensory scores for the 10 times diluted solution compared to the original undiluted product. These results are consistent with the discussion and data presented in Example 8, which indicate that a surfactant of low CMC lowers the PBI of the perfume and can greatly reduce the expected "perfume burst" upon dilution.

The panel studies indicate that this "perfume burst" upon dilution can be perceived quite easily by the human nose if the formulation is designed according to the rules listed in this invention.

TABLE 7

Sample Information of the Single Perfume (γ-methyl-ionone) System for Panel Study

| Sample Name | Information |
|---|---|
| 1 | 0.0649 wt. % γ-methyl-ionone in 4.5 wt. % sodium laurate |
| 2 | 10 times dilution of 0.0649 wt. % γ-methyl-ionone in 4.5 wt. % sodium laurate |
| 3 | 0.2193 wt. % γ-methyl-ionone in 4.5 wt. % sodium laurate |
| 4 | 10 times dilution of 0.2193 wt. % γ-methyl-ionone in 4.5 wt. % sodium laurate |
| 5 | 0.2200 wt. % γ-methyl-ionone in 4.5 wt. % SLES |
| 6 | 10 times dilution of 0.2200 wt. % γ-methyl-ionone in 4.5 wt. % SLES |

TABLE 8

Sample Information of the Multi-Component Perfume (menthone, tetra-hydro-linalool, α-ionone, γ-methyl-ionone) System for Panel Study

| Sample Name | Information |
|---|---|
| 7 | 0.2404 wt. % perfume mixture in 5 wt. % sodium laurate |
| 8 | 10 times dilution of 0.2404 wt. % perfume mixture in 5 wt. % sodium laurate |
| 9 | 0.6022 wt. % perfume mixture in 5 wt. % sodium laurate |
| 10 | 10 times filution of 0.6022 wt. % perfume mixture in 5 wt. % sodium laurate |
| 11 | 0.2433 wt. % perfume mixture in 5 wt. % SLES |
| 12 | 10 times dilution of 0.2433 wt. % perfume mixture in 5 wt. % SLES |

Example 12

There are any number of surfactant containing formulations that should provide a "perfume burst" in use. These include personal wash products (i.e. shower gels, soap bars), shampoos, household cleaners, light duty detergents, fabric washing products, etc. All of these products undergo some dilution with use which could potentially cause release of fragrance molecules from the surfactant micelles and provide a "burst" of fragrance intensity. As explained in the previous examples, the CMC of the surfactant mixture, the amount of surfactant in the product and the perfume ingredients used in the fragrance formulation all contribute to the type and intensity of the "perfume burst" during product use. The following formulations are just a few examples of products that would be expected to provide a "fragrance burst" or change in fragrance note, assuming the perfume was properly designed (i.e. a fragrance containing a fraction of components with high PBI values).

TABLE 9

| Formulation Ingredients (%) | Form. #1 | Form. #2 | Form. #3 | Form. #4 | Form. #5 | Form. #6 | Form. #7 | Form. #8 |
|---|---|---|---|---|---|---|---|---|
| Sodium Laurate | 10 | 5 | 8 | 4 | | | 4 | 5 |
| TEA Laurate | | 5 | | | 5 | | | |
| Sodium Laureth Sulfonate | | | 2 | | 4 | | | 8 |
| Sodium Lauryl Sulfate | | | | | | 8 | | |
| Alkylpoly Glucoside | | | | 7 | | | | |
| Nonionic Polymeric Surfactant Containing Mixture of Alkylene Oxides | | 2 | | 5 | | | | |
| Caprylamido Propylbetaine | 1 | | | | 1 | 2 | | 1 |
| Sodium Cocoylisethionate | | | | | | | 10 | |
| Lauric Acid | 3 | | 2 | 2 | | | 3 | |
| Amine Oxide | | | | | | 1 | | |
| Xanthan Gum | | 1 | | | | | | 0.8 |
| Jaguar S13 (Cationic Polymer) | | | | | 0.4 | | | |
| Polyacrylates (e.g., Structuring Agent) | 0.6 | | 0.6 | | | | | |
| Polymer JR (Cationic Polymer) | | | | | | | 0.3 | |
| Triclosan | | 0.5 | | | | | | |
| Trichlorocarbanilide | | | | 0.5 | | | | |
| Propylene Glycol | | | | | | | | 10 |
| Glycerine | | | | | | | 30 | |
| Vitamin E | | | | | 0.05 | | | |
| Perfume | 1 | 1 | 1.3 | 1 | 1 | 1.2 | 0.8 | 1 |
| Water | To 100 | To 100 | To 100 | To 100 | To 100 | To 100 | To 100 | To 100 |

As noted, these are examples of the many formulations in which the perfume burst concept can be used.

What is claimed is:

1. Compositions yielding a maximum fragrance burst of one or more of the fragrance components of at least 20%, relative to an undiluted product, wherein said composition is defined by perfume burst index PBI:

$$PBI = \frac{\phi - 1.4/CMC}{K}$$

wherein $\phi$=oil/water partition coefficient of a selected perfume or perfume components in a mixture;

CMC=critical micellization concentration (wt./wt.) of selected surfactant system or mixture of surfactant system in diluent or continuous phase;

K=volatility constant of selected perfume from said continuous phase or diluent (atmospheres);

wherein said perfume or at least one component of said perfume mixture and wherein said surfactant system or said mixture of surfactant systems are selected such that variables are calculated to provide a PBI that is greater than about 3; wherein by maximum fragrance burst of at least 20% is meant that the perfume concentration in the headspace above said fragrance or fragrance components increases at least 20% relative to the perfume concentration in the headspace of an undiluted product comprising the same fragrance or fragrance components measured as the composition comprising said fragrance or fragrance components is diluted below the critical micelle concentration (CMC) of the fragrance, surfactant and water system.

2. A composition according to claim 1, wherein said perfume is a type 2 perfume selected to have an oil/water partition coefficient greater than about 500 and volatility constant of less than about 20.

3. A composition according to claim 2, wherein said perfume is selected from the group consisting of allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl acetate, citronellyl isobutyrate, citronellyl propionate, cuminic aldehyde, cyclohexylsalicylate, cyclamen aldehyde, cyclomyral, dihydro isojamonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super™ (7-acettl,1,2,3,4,5,6,7,8-octahydro,1,1,6,7-tetramethyl napthalene), cis-jasmine, lilial, linalyl benzoate, 20 methoxy naphthaline, methyl cinnamate, methyl eugenol, γ-methylionone, methyl linolate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara, ylangene, and mixtures thereof.

4. A composition according to claim 1, wherein said perfume is a type 3 perfume selected to have a partition coefficient of greater than about 500 and volatility constant of about 20 to about 1000.

5. A composition according to claim 4, wherein said perfume is selected from the group consisting of allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, and mixtures thereof.

6. A composition according to claim 1 yielding maximum fragrance burst of at least 25%.

7. A composition according to claim 1, wherein said surfactant or mixture of surfactant system has CMC greater than about 0.0001 wt. to wt., said weight percent representing percent of surfactant as percent of total surfactant composition required for micelles to be present in said surfactant composition.

8. A composition according to claim 1, wherein surfactant systems contain surfactants selected from the group consisting of sodium lauryl ether sulfate, sodium laurate, potassium laurate, sodium oleate, potassium oleate, triethanolamine laurate, alkylpolyglucosides, sodium lauryl sulfate, caprylamidopropyl betaine, sodiumcocoylisethionate and mixtures thereof.

9. A composition according to claim 8, wherein the diluent or continuous phase in which said surfactant systems or surfactant system mixtures is found additionally comprises CMC modifying ingredients selected from the group consisting of urea; glycerine; C1–C12 straight-chained or branched alcohols or diols; water soluble polymers selected from polyvinylpyrolidone, polyvinylalcohol, polyethyleneglycol, polypropyleneglycol; multivalent electrolytes selected from magnesium, calcium and aluminum salts; sugars selected from dextrose, glucose, maltose, galactose, sucrose and mixtures thereof.

* * * * *